(12) United States Patent
Agusti et al.

(10) Patent No.: US 10,509,028 B2
(45) Date of Patent: Dec. 17, 2019

(54) USE OF A LOW-DENSITY IMMISCIBLE COMPOUND IN A DEVICE FOR DETECTING AN ANALYTE IN A SAMPLE

(71) Applicant: BIO-RAD EUROPE GMBH, Basel (CH)

(72) Inventors: Julien Agusti, Cressier FR (CH); Stephane Bombard, Cressier FR (CH); Frederic Buffiere, Marnes la Coquette (FR)

(73) Assignee: BIO-RAD EUROPE GMBH, Basel (CH)

( * ) Notice: Subject to any disclaimer, the term of this patent is extended or adjusted under 35 U.S.C. 154(b) by 0 days.

(21) Appl. No.: 15/574,852

(22) PCT Filed: May 18, 2016

(86) PCT No.: PCT/EP2016/061158
§ 371 (c)(1),
(2) Date: Nov. 17, 2017

(87) PCT Pub. No.: WO2016/184924
PCT Pub. Date: Nov. 24, 2016

(65) Prior Publication Data
US 2018/0128818 A1  May 10, 2018

(30) Foreign Application Priority Data
May 19, 2015  (EP) .................................... 15305748

(51) Int. Cl.
*G01N 33/538*  (2006.01)
*G01N 33/53*  (2006.01)
(Continued)

(52) U.S. Cl.
CPC .......... *G01N 33/5304* (2013.01); *B01L 3/502* (2013.01); *B01L 3/50215* (2013.01);
(Continued)

(58) Field of Classification Search
None
See application file for complete search history.

(56) References Cited

U.S. PATENT DOCUMENTS 5,460,940 A    10/1995  Yves et al.
6,121,055 A *   9/2000  Hargreaves ............. B01L 3/502
                                                            435/2

(Continued)

FOREIGN PATENT DOCUMENTS

EP      0 100 588    2/1984

OTHER PUBLICATIONS

Written Opinion in International Application No. PCT/EP2016/061158, dated Jun. 30, 2016, pp. 1-10.

*Primary Examiner* — Christopher L Chin
(74) *Attorney, Agent, or Firm* — Saliwanchik, Lloyd & Eisenschenk

(57) ABSTRACT

The present disclosure relates to a device for detecting an analyte in a sample, and especially for detecting antigen/antibody reactions, wherein said device comprises a layer composed of a low-density immiscible compound. The disclosure also relates to a method for detecting an analyte in a sample and especially for detecting antigen/antibody reactions in a device comprising a layer composed of a low-density immiscible compound. The disclosure further relates to the uses of such low-density immiscible compound.

12 Claims, 16 Drawing Sheets

(51) Int. Cl.
*G01N 33/543* (2006.01)
*B01L 3/00* (2006.01)
*G01N 33/80* (2006.01)
*G01N 35/00* (2006.01)

(52) U.S. Cl.
CPC ....... *G01N 33/5306* (2013.01); *G01N 33/538* (2013.01); *G01N 33/54366* (2013.01); *G01N 33/80* (2013.01); *G01N 35/00069* (2013.01); *B01L 2200/142* (2013.01); *B01L 2300/0832* (2013.01); *G01N 2035/00148* (2013.01)

(56) References Cited

U.S. PATENT DOCUMENTS

| | | | |
|---|---|---|---|
| 8,257,925 B2* | 9/2012 | Brown | B01L 3/5027 |
| | | | 435/6.1 |
| 8,993,243 B2* | 3/2015 | Beebe | G01N 33/54326 |
| | | | 435/6.19 |
| 2009/0136963 A1* | 5/2009 | Breidenthal | B01F 11/0045 |
| | | | 435/6.11 |
| 2013/0029321 A1* | 1/2013 | Hansen | B01L 3/50273 |
| | | | 435/5 |
| 2014/0057271 A1* | 2/2014 | Kelso | C12N 15/1006 |
| | | | 435/6.12 |

* cited by examiner

|  | Neg. sample (AB Serum) | | | Weakly pos. sample (anti-RH4) | | |
|---|---|---|---|---|---|---|
| Anti-IgG card Frozen R1r cells | | | | | | |
| Condition | CTRL (no oil) | 5 µL oil | 10 µL oil | CTRL (no oil) | 5 µL oil | 10 µL oil |
| Result | - | - | - | 2+ | 2+ | 2+ |

Figure 3

|  | 0h-storage at 56°C | | | | | 4h-storage at 56°C | | | | | 24h-storage at 56°C | | | | |
|---|---|---|---|---|---|---|---|---|---|---|---|---|---|---|---|
| L-DIC Vol. | Ctl | 3 µL | 4 µL | 5 µL | 10 µL | Ctl | 3 µL | 4 µL | 5 µL | 10 µL | Ctl | 3 µL | 4 µL | 5 µL | 10 µL |
| Visual | - | - | - | - | - | ++++ | - | - | - | - | ++++ | - | - | - | - |

Figure 4

| | CTRL (air gap) | No air gap | No air gap + 5 µL oil |
|---|---|---|---|
| LISS/Coombs + Pool R1r + Diluent 2 + weak anti-RH4 | After dispense ||||
| Visual | /  /  | /  /  | /  /  |
| LISS/Coombs + Pool R1r + Diluent 2 + weak anti-RH4 | After centrifugation ||||
| Visual | 2  2 | -  - | 2  2 |

Figure 5

| | Before shaking | After shaking | After 10 min centrifugation |
|---|---|---|---|
| Anti-IgG Card | | | |
| L-DIC | Ctl \| liquid L-DIC \| solid L-DIC | Ctl \| liquid L-DIC \| solid L-DIC | Ctl \| liquid L-DIC \| solid L-DIC |

Figure 6

|  | Immediately after dispense | | | | | | After 15 min incubation at 37°C | | | | | |
|---|---|---|---|---|---|---|---|---|---|---|---|---|
| LISS/COOMBS Pool R1r in ID-Diluent2 | | | | | | | | | | | | |
| Oil Volume | CTL | CTL | 5 µL | 5 µL | 50 µL | 50 µL | CTL | CTL | 5 µL | 5 µL | 50 µL | 50 µL |

|  | Weak anti-RH4 | | | | | | AB-Serum | | | | | |
|---|---|---|---|---|---|---|---|---|---|---|---|---|
| LISS/COOMBS Pool R1r in ID-Diluent2 | | | | | | | | | | | | |
| Oil Volume | CTL | CTL | 5 µL | 5 µL | 50 µL | 50 µL | CTL | CTL | 5 µL | 5 µL | 50 µL | 50 µL |
| Reader | ++ | ++ | ++ | ++ | ++ | ++ | - | - | - | - | - | - |
| Visual | 2 | 2 | 2 / 2+ | 2 / 2+ | 2 | 2 | - | - | - | - | - | - |

Figure 9

| | Prior testing | | | | | | | |
|---|---|---|---|---|---|---|---|---|
| LISS/COOMBS Pool R1r in ID-Diluent2 | | | | | | | | |
| | Ø | | Mineral oil | | Octadecane | | Nonadecane | |
| Volume | Ø | Ø | 5 µL | 5 µL | 5 µL | 5 µL | 5 µL | 5 µL |

| | After Centrifugation | | | | | | | |
|---|---|---|---|---|---|---|---|---|
| LISS/COOMBS Pool R1r in ID-Diluent2 | | | | | | | | |
| | Ø | | Mineral oil | | Octadecane | | Nonadecane | |
| Volume | Ø | Ø | 5 µL | 5 µL | 5 µL | 5 µL | 5 µL | 5 µL |
| Saxo | - | - | - | - | - | - | - | - |
| Visual | - | - | - | - | - | - | - | dtx |

Figure 10

| | After Centrifugation | | | | | | | |
|---|---|---|---|---|---|---|---|---|
| LISS/COOMBS Pool R1r in ID-Diluent2 | | | | | | | | |
| | Ø | | Mineral oil | | Octadecane | | Nonadecane | |
| Volume | Ø | Ø | 5 µL | 5 µL | 5 µL | 5 µL | 5 µL | 5 µL |
| Saxo | ++ | ++ | ++ | ++ | ++ | ++ | ++ | ++ |
| Visual | 2/2- | 2/2- | 2/2+ | 2/2+ | 2/2+ | 2/2+ | 2/2+ | 2/2+ |

Figure 11

| 5 min incubation before testing | | | | | | | | | |
|---|---|---|---|---|---|---|---|---|---|
| Sample | QC6 | | | QC7 | | | QC8 | | |
| octadecane volume | ∅ | 5μL | 5μL | ∅ | 5μL | 5μL | ∅ | 5μL | 5μL |
| decane volume | ∅ | ∅ | 5μL | ∅ | ∅ | 5μL | ∅ | ∅ | 5μL |
| Saxo | - | ∅ | - | ++ | ∅ | ++ | +++ | ∅ | +++ |
| Visual | ./- | ∅ | ./- | 2+ | ∅ | 3- | 3 | ∅ | 3 |

| 10 min incubation before testing | | | | | | | | | |
|---|---|---|---|---|---|---|---|---|---|
| Sample | QC6 | | | QC7 | | | QC8 | | |
| octadecane volume | ∅ | 5μL | 5μL | ∅ | 5μL | 5μL | ∅ | 5μL | 5μL |
| decane volume | ∅ | ∅ | 5μL | ∅ | ∅ | 5μL | ∅ | ∅ | 5μL |
| Saxo | - | ∅ | - | ++ | ∅ | ++ | +++ | ∅ | +++ |
| Visual | ./- | ∅ | ./- | 2+ | ∅ | 3- | 3 | ∅ | 3 |

Figure 13

| A1<br>Reverse cell<br><br>10 min<br>incub RT | | | | | | |
|---|---|---|---|---|---|---|
| Reverse cells | AB Group | | | O Group | | |
| octadecane volume | ∅ | 5µL | 5µL | ∅ | 5µL | 5µL |
| decane volume | ∅ | ∅ | 5µL | ∅ | ∅ | 5µL |
| Saxo | - | ∅ | - | ++++ | ∅ | ++++ |
| Visual | - | ∅ | ./- | 3+ | ∅ | 4 |

| B<br>Reverse Cell<br><br>10 min<br>incub RT | | | | | | |
|---|---|---|---|---|---|---|
| Reverse cells | AB Group | | | O Group | | |
| octadecane volume | ∅ | 5µL | 5µL | ∅ | 5µL | 5µL |
| decane volume | ∅ | ∅ | 5µL | ∅ | ∅ | 5µL |
| Saxo | - | ∅ | - | ++++ | ∅ | ++++ |
| Visual | - | ∅ | - | 4- | ∅ | 4 |

| O<br>reverse cell<br><br>10 min<br>incub RT | | | | | | |
|---|---|---|---|---|---|---|
| Reverse cells | AB Group | | | O Group | | |
| octadecane volume | ∅ | 5µL | 5µL | ∅ | 5µL | 5µL |
| decane volume | ∅ | ∅ | 5µL | ∅ | ∅ | 5µL |
| Saxo | - | ∅ | - | - | ∅ | - |
| Visual | - | ∅ | - | - | ∅ | - |

Figure 14

Results

| | Card with 5 µl Oil |||||||||| | |
|---|---|---|---|---|---|---|---|---|---|---|---|---|
| ID-HbS Sickle Cell Test | | | | | | | | | | | | |
| No | 1 | 2 | 3 | 4 | 5 | 6 | 7 | 8 | 9 | 10 | Dia cell I | Dia cell II |
| Visual | - | - | - | - | - | - | - | - | - | - | 4- DP | 4- DP |
| Saxo | - | - | - | - | - | - | - | - | - | - | ? | ? |

| | No Oil |||||||||| | |
|---|---|---|---|---|---|---|---|---|---|---|---|---|
| ID-HbS Sickle Cell Test | | | | | | | | | | | | |
| No | 1 | 2 | 3 | 4 | 5 | 6 | 7 | 8 | 9 | 10 | Dia cell I | Dia cell II |
| Visual | - | - | - | - | - | - | - | - | - | - | 3+ DP | 3+ DP |
| Saxo | - | - | - | - | - | - | - | - | - | - | ? | ? |

Figure 15

Specificity: Negative samples: Plasmas and Serums from SRK
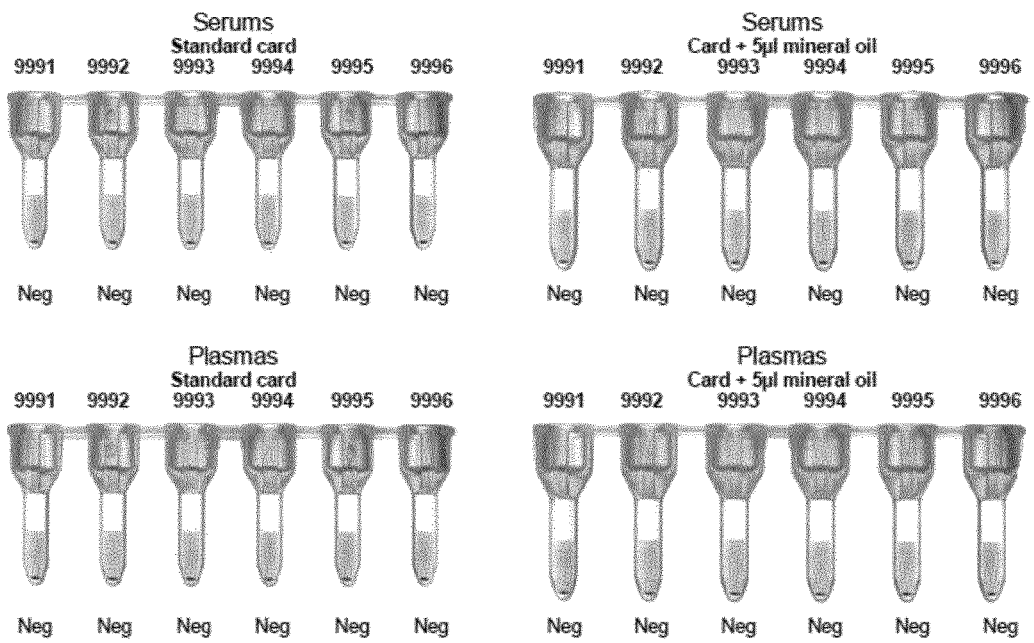
Sensitivity:
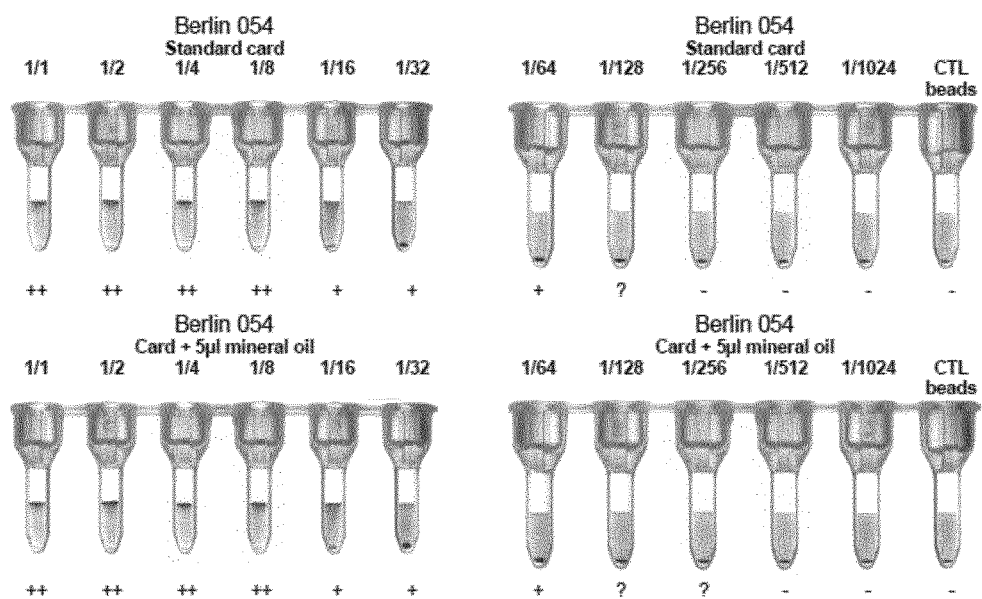
Figure 16

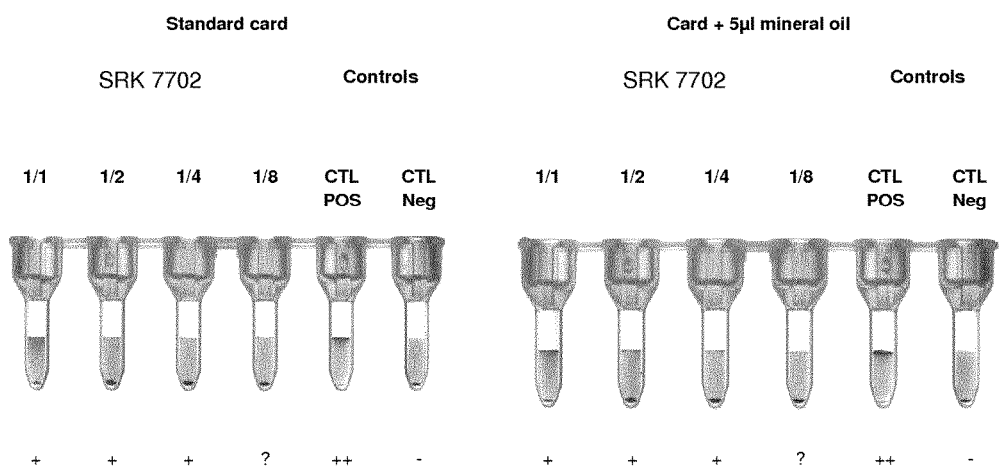
Figure 16 (continuation)

Specificity: SRK samples: Positive results
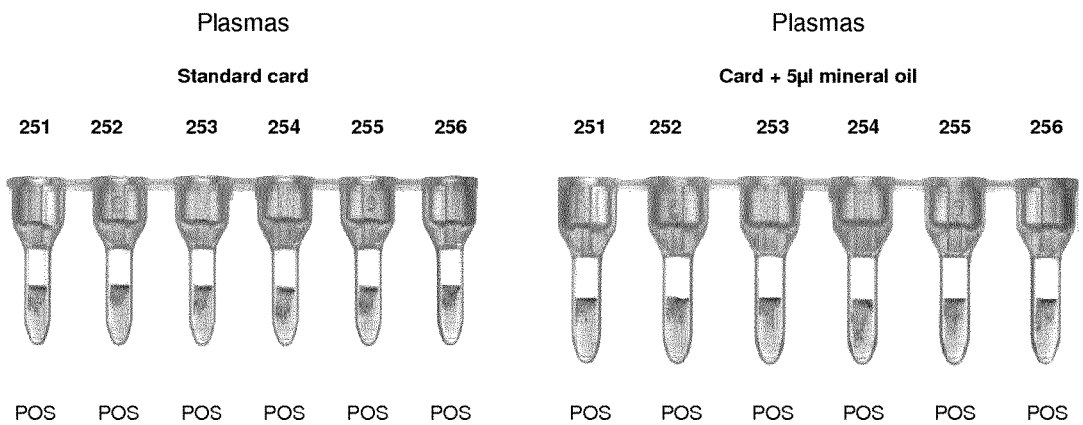
Specificity: IgA deficiency samples: Negative results
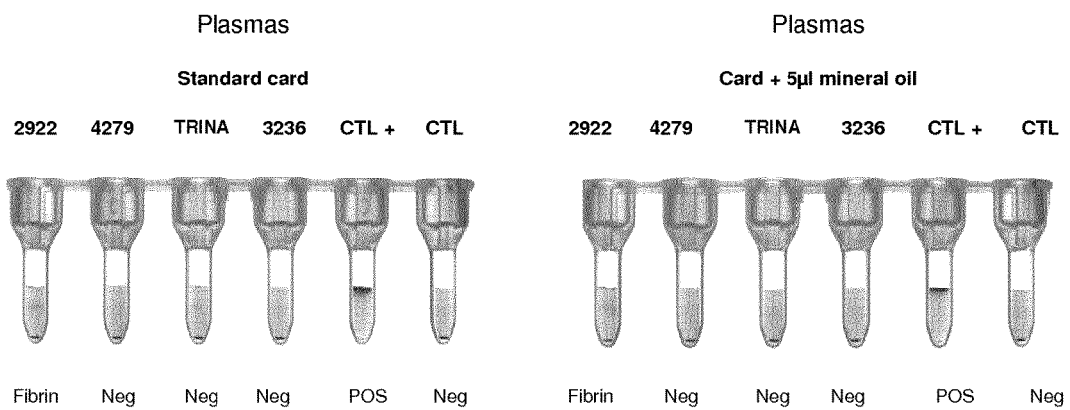
Figure 17

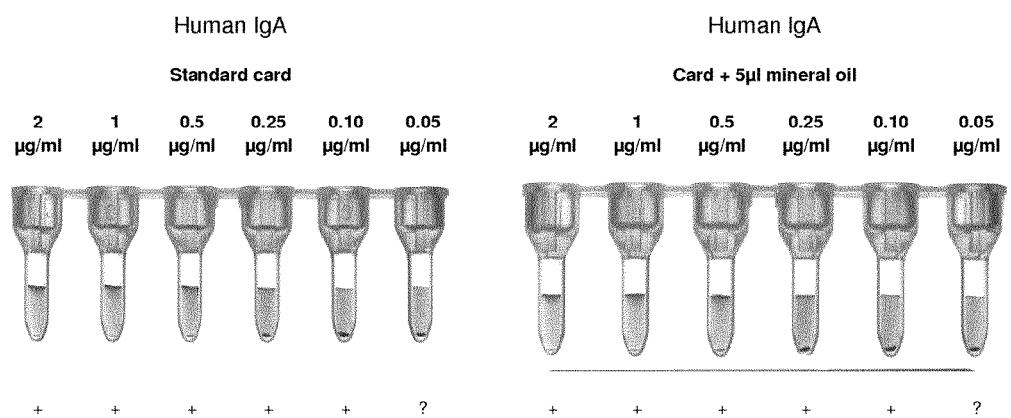
Figure 17 (continuation)

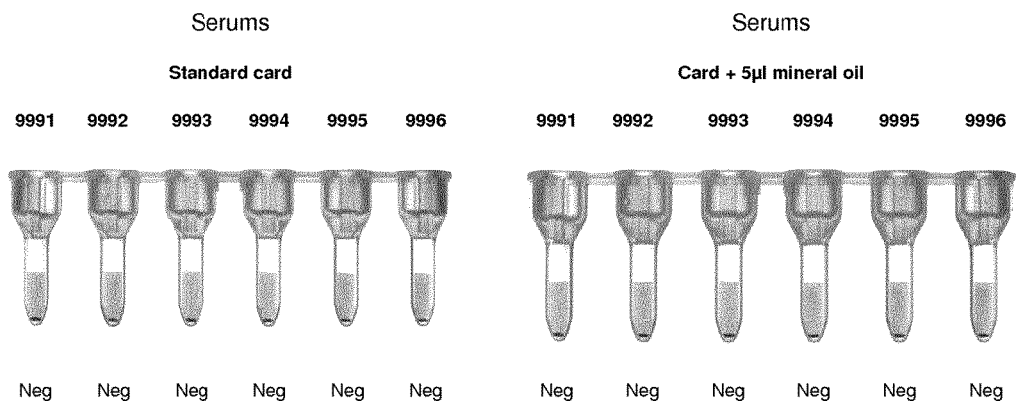
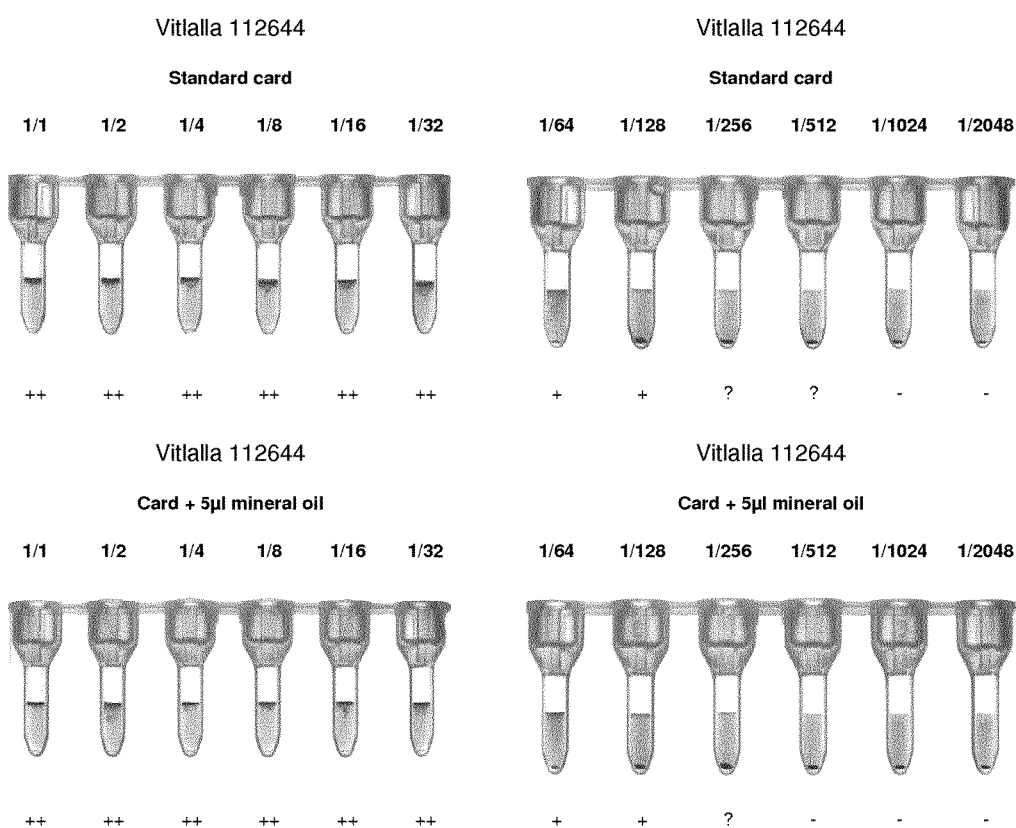
Figure 18

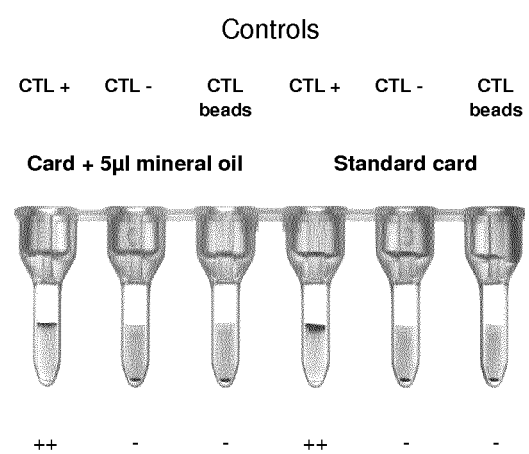
Figure 18 (continuation)

USE OF A LOW-DENSITY IMMISCIBLE COMPOUND IN A DEVICE FOR DETECTING AN ANALYTE IN A SAMPLE

CROSS-REFERENCE TO RELATED APPLICATIONS

This application is the U.S. national stage application of International Patent Application No. PCT/EP2016/061158, filed May 18, 2016, which claims priority to European Application EP15305748.4, filed May 19, 2015, the disclosures of which are hereby incorporated by reference in their entirety.

FIELD OF THE DISCLOSURE

The present disclosure relates to a device for detecting an analyte in a sample, wherein said device comprises a layer composed of a low-density immiscible compound. It also relates to a method for detecting an analyte in a sample by using a device comprising a layer composed of a low-density immiscible compound. It further relates to the uses of such low-density immiscible compound.

BACKGROUND

Column Agglutination Test ("CAT" or "gel card" or "reagent card") is one of the most common formats used in the field of immunohematology. Gel card is composed of a plurality of microtubes. This system for typing and screening blood is based on the sieving effect of a separation matrix. The test is typically performed in a microcolumn in which the red cell agglutinates are trapped in the separation matrix during centrifugation (in case of reaction between antigens and antibodies), and unagglutinated cells form a pellet at the bottom of the column (in the absence of reaction).

Cards are easy-to-use, easy-to-read and provide reliable results when used both manually and with automatic analyzers. However, storage of cards (generally at room temperature) induces a normal evaporation of supernatant. This shortens the shelf life of cards. The evaporated material condenses on the underside of the cover of the cards. Evaporation further leads to a lack of performance and stability. Additionally, abnormal transport conditions (the, mic stress, excessive shaking . . . ) could accelerate the degradation. In addition, for some tests such as Indirect Antiglobulin Test, samples and additional reagents (also referred to herein as the reactive medium) added into the reaction chamber of card are preferably physically separated from the gel (also referred to herein as the separation matrix) and the supernatant having anti-human globulin to achieve optimum performance and to avoid that a "neutralization phenomenon" occurs between the anti-human globulin and the sample, leading to weakened or falsely negative reactions. The gel and the supernatant mare referred hereinafter to as the reaction medium. One way to accomplish the physical separation between the reaction chamber and the reaction medium is by maintaining an airgap between the reaction medium and the reagents added to the reaction chamber. The absence of this air gap between gel and reactive medium may lead to decreased performance (Bobryk S. (2011). Variation in pipetting may lead to the decreased detection of antibodies in manual gel testing (Clinical Laboratory Science, 161-166) during Indirect Antiglobulin Test.

SUMMARY

It has been unexpectedly discovered that the addition of a layer of a low-density immiscible compound in devices for detecting an analyte in a sample and especially for detecting antigen/antibody reactions such as gel cards overcomes the above mentioned problems (see examples). In addition, such compound also facilitates manual or automated distribution of the reagents and/or samples to be tested in the device, increases the throughput, reduces contamination, and allows encapsulation of reagents inside cards. Further advantages of such low-density immiscible compound will be further discussed.

Disclosed is a device for detecting an analyte in a sample, and especially a device for detecting analyte/ligand reactions, wherein said device comprises:
  a reaction chamber able to receive the sample to be tested; and
  a reaction medium comprising reagents, said reagents comprising a separation matrix;
  the reaction chamber lying above the reaction medium within the device;
  the reaction chamber and/or the reaction medium optionally comprising reagents, said reagents comprising an analyte ligand; and
  the device further comprising a layer composed of a low-density immiscible compound that separates the reaction chamber from the reaction medium.

Also disclosed is a method for detecting an analyte in a sample, wherein:
  a) a device is provided, wherein the device comprises:
    a reaction chamber able to receive the sample to be tested; and a reaction medium comprising reagents, said reagents comprising a separation matrix;
    the reaction chamber lying above the reaction medium within the device;
    the reaction chamber and/or the reaction medium optionally comprising reagents, said reagents comprising an analyte ligand; and
    the device further comprising a layer composed of a low-density immiscible compound that separates the reaction chamber from the reaction medium;
  b) the sample to be tested and, optionally, reagents comprising an analyte ligand are dispensed into the reaction chamber of the device; and
  c) the sample or the mixture of sample and analyte ligand is subsequently exposed to sedimentation by gravitation and/or centrifugation in the reaction medium;
    wherein reagents comprising an analyte ligand are provided at least at step a) and/or at step b), and
  wherein if an analyte/ligand complex is formed, such mixture lies on or within the separation matrix and in the absence of such complex, the mixture lies beneath the separation matrix, the entire reaction being carried out in the device.

In an embodiment, a device for detecting an analyte in a sample comprises a reaction chamber configured to receive the sample to be tested; a separation matrix; and a layer composed of a low-density immiscible compound that separates the reaction chamber from the separation matrix, wherein the reaction chamber is located above the separation matrix within the device. In some embodiments, the separation matrix and/or the reaction chamber comprises an analyte ligand. In certain embodiments, the analyte ligand is an antibody, an antibody fragment, or an antigen.

In some embodiments, the low-density immiscible compound has a lower density than the density of the separation matrix. In some embodiments, the low-density immiscible compound has a density of less than 1, and/or is hydrophobic. In some embodiments, the low-density immiscible compound is chosen from or is provided as a composition comprising one or several compounds chosen from: synthetic oil, organic oil, mineral oil, paraffinic oil, paraffin such as liquid paraffin, non-polar solvents, fatty acids, for example stearic acid, alkanes mixture and pure alkane such as decane, undecane, dodecane, tridecane, tetradecane, pentadecane, hexadecane, heptadecane, octadecane, nonadecane, eicosane or heneicosane. In certain embodiments, the low-density immiscible compound comprises mineral oil. In some embodiments, the low-density immiscible compound comprises nonadecane, octadecane or a combination thereof. In some embodiments, the low-density immiscible compound further comprises decane. In some embodiments, the low-density immiscible compound is liquid or solid at room temperature. In certain embodiments, if the low-density immiscible compound is solid, such solid compound is further liquefied thermally or chemically.

In some embodiments, the low-density immiscible compound separates the separation matrix from the reaction chamber in the device. In some embodiments, the device does not comprise any air gap between the separation matrix and the low-density immiscible compound. In certain embodiments, the reaction chamber comprises reagents, the reagents comprising an analyte ligand, and further comprises a layer composed of a low-density immiscible compound which lies on top of the reagents, and separates the reagents, or any reagent present in the reaction chamber, from air. In some embodiments, the low-density immiscible compound encapsulates a reagent and/or the sample.

In an embodiment, a method for detecting an analyte in a sample includes (a) providing a device comprising a reaction chamber configured to receive the sample to be tested; a separation matrix; and a layer composed of a low-density immiscible compound that separates the reaction chamber from the separation matrix, wherein the reaction chamber is located above the separation matrix within the device; (b) dispensing the sample to be tested into the reaction chamber of the device; and (c) exposing the device to sedimentation by gravitation and/or centrifugation, wherein reagents comprising an analyte ligand are provided at least at step (a) and/or at step (b), wherein if an analyte-ligand complex is formed, such mixture lies on or within the separation matrix and in the absence of such complex, the mixture lies beneath the separation matrix, the entire reaction being carried out in the device.

In an embodiment, a kit for detecting an analyte in a sample comprises a device comprising a reaction chamber configured to receive the sample to be tested; a separation matrix; and a layer composed of a low-density immiscible compound that separates the reaction chamber from the separation matrix, wherein the reaction chamber is located above the separation matrix within the device. In some embodiments, the kit further comprises an analyte ligand in the separation matrix and/or the reaction chamber. In some embodiments, the kit further comprises instructions for performing a method to detect an analyte in a sample.

BRIEF DESCRIPTION OF THE FIGURES

FIG. 3 illustrates the results of a test of biocompatibility with a low-density immiscible compound according to one embodiment.

FIG. 4 illustrates the results of a test of evaporation with a low-density immiscible compound ("L-DIC") according to one embodiment.

FIG. 5 illustrates the results of a test of neutralization-robustness as compared to air gap with a low-density immiscible compound according to one embodiment.

FIG. 6 illustrates the results of a test of integrity of gel and supernatant with a low-density immiscible compound according to one embodiment.

FIG. 9 illustrates the results of a test of facilitation of dispense with a low-density immiscible compound according to one embodiment.

FIGS. 10 and 11 illustrate the results of a test of "thermally dependent modular cover plate" with low-density immiscible compounds according to one embodiment.

FIG. 13: illustrates the results of a test of "chemically dependent modular cover plate" with low-density immiscible compounds according to one embodiment (part alkanes in DAT) (QC means Quality Controls).

FIG. 14: illustrates the results of a test of "chemically dependent modular cover plate" with low-density immiscible compounds according to one embodiment (part alkanes in reverse).

FIG. 15: illustrates the results of a test on the effect of a low-density immiscible compound as disclosed herein on an ID-HbS card.

FIG. 16: illustrates the results of a test on the effect of a low-density immiscible compound as disclosed herein on an ID-PaGIA IgA deficiency test.

FIG. 17: illustrates the results of a test on the effect of a low-density immiscible compound as disclosed herein on an ID-PaGIA anti-IgA antibody test.

FIG. 18: illustrates the results of a test on the effect of a low-density immiscible compound as disclosed herein on ID-PaGIA Syphilis test.

DETAILED DESCRIPTION

Figure 1:
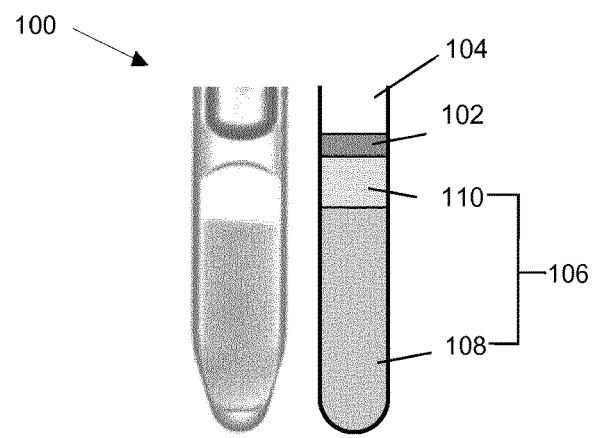
FIG. 1 illustrates a device having a low-density immiscible compound layer according to one embodiment.

Disclosed is a device for detecting an analyte in a sample. When the device is a gel card, a low-density immiscible compound 102 as disclosed herein separates the reaction chamber 104 from the reaction medium 106 of the microtube gel card. In microtubes 100 of gel cards, the microtube 100 generally contains at least 2 phases: the gel 108 and the supernatant 110 (both of which comprise the reaction medium 106). In a particular embodiment, the main objective is then to separate physically by the layer composed of a low-density immiscible compound 102 as disclosed herein, reaction medium 106 in the microtube 100 from the reaction chamber 104 in order to prevent supernatant evaporation and thus to increase shelf life. See FIG. 1.

In an embodiment, a device 100 comprises a reaction chamber 104 configured to receive the sample to be tested; a separation matrix 108; and a layer composed of a low-density immiscible compound 102 that separates the reaction chamber 104 from the separation matrix 108, wherein the reaction chamber 104 is located above the separation matrix 108 within the device 100.

In some embodiments, the disclosed device 100 with low-density immiscible compound 102 provides one or more of the following benefits:
  prevents the evaporation of the reagents of the reaction medium 106, in particular the evaporation of supernatant 110 in the microtube 100 of gel cards; and/or
  prevents the neutralization and/or consumption of the reagents (e.g., antibodies or antigens) of the reaction chamber 104 and/or of the reaction medium 106 which can give a false negative or incorrect result; and/or
  does not interact/interfere with the sample (e.g., red blood cells, antibodies) and reagents (e.g., antibodies) used in the test; and/or
  enhances the reactivity of positive reaction without altering the specificity; and/or
  facilitates the distribution of the reagents and the sample to be tested into the device 100, in particular allowing the dispense of the reagents (if any in the reaction chamber 104) and the samples to be tested anywhere in the reaction chamber 104; and/or
  confines, before the analytical process, the reagents of the reaction medium 106 within the reaction medium 106 and especially at the bottom part of the reaction medium 106 (which may be the bottom part of the device 100) and prevents them from spreading into the reaction chamber 104 in case of shocks or reversal; and/or
  allows, during the analytical process, the passage of the reagents (if any in the reaction chamber 104) and of the sample to be tested from the reaction chamber 104 through the reaction medium 106 (which may lie at the bottom part of the device 100); and/or
  confines, after the analytical process, all the reagents and the sample to be tested in the reaction medium 106.

Also provided is a method for detecting an analyte in a sample such as a method for detecting analyte/ligand reactions, and especially a method for detecting an antigen and/or an antibody in a sample, wherein:
  a) a device 100 is provided, which comprises (i) a reaction chamber 104 able to receive the sample to be tested, and (ii) a reaction medium 106 comprising reagents, said reagents comprising a separation matrix 108, wherein the reaction chamber 104 lies above the reaction medium 106 within the device 100, and wherein, optionally, the reaction chamber 104 and/or the reaction medium 106 comprises reagents, said reagents comprising an analyte ligand,
  b) the sample to be tested and, optionally, reagents comprising an analyte ligand are dispensed into the reaction chamber 104; and
  c) the sample or the mixture of sample and analyte ligand is subsequently exposed to sedimentation by gravitation in the reaction medium 106;
wherein if an analyte/ligand complex is formed, such mixture lies on or within the separation matrix 108, and in the absence of such complex, the mixture lies beneath the separation matrix 108, the entire reaction being carried out in the device 100,
and wherein a layer composed of a low-density immiscible compound 102 separates the reaction chamber from the reaction medium within the device.

Alternatively, in the provided method, at step c), the sample or the mixture of sample and analyte ligand is subsequently exposed to sedimentation in the reaction medium 106 by centrifugation.

Alternatively again, in the provided method, at step c), the sample or the mixture of sample and analyte ligand is subsequently exposed to sedimentation by centrifugation and gravitation (e.g., sequentially, in any order) in the reaction medium 106.

Hence, in the method described herein, reagents comprising an analyte ligand are provided at least at step a) and/or at step b).

In a particular embodiment, in step a), the reaction chamber 104 and/or the reaction medium 106 comprise(s) reagents, said reagents comprising an analyte ligand. In this embodiment, additional reagents comprising an analyte ligand may or may not be dispensed into the reaction chamber 104 at step b).

In another particular embodiment, neither the reaction chamber 104 nor the reaction medium 106 of the device 100 provided at step a) comprises reagents, said reagents comprising an analyte ligand, said reagents being provided in the device 100 at step b).

When reagents comprising an analyte ligand are dispensed into the reaction chamber 104 in step b), the dispensing of a sample can be performed before, after, or at the same time as the dispense of reagents comprising an analyte ligand.

In a particular embodiment, "performed at the same time" means that in step b), a sample to be tested is mixed with reagents comprising an analyte ligand, and the resulting mixture (the reactive medium 112) is then dispensed into the reaction chamber 104 of the device 104. See FIG. 2.

In a particular embodiment, the provided method comprises the following steps:
  a) a device 100 is provided, which comprises (i) a reaction chamber 104 comprising reagents, said reagents comprising an analyte ligand and (ii) a reaction medium 106 comprising reagents, said reagents comprising a separation matrix 108, wherein the reaction chamber 104 lies above the reaction medium 106, and wherein a layer composed of a low-density immiscible compound 102 separates the reaction chamber 104 from the reaction medium 106;
  b) a sample to be tested is brought into contact with the reagents in the reaction chamber 104 of the device 100; and
  c) the mixture of sample and analyte ligand is subsequently exposed to sedimentation by gravitation in the reaction medium 106;
wherein if an analyte/ligand complex is formed, such mixture lies on or within the separation matrix 108 and in the absence of such complex, the mixture lies beneath the separation matrix 108, the entire reaction being carried out in the device 100.

Alternatively, in the method provided above, at step c), the sample or the mixture of sample and analyte ligand is subsequently exposed to sedimentation in the reaction medium 106 by centrifugation.

Alternatively again, in the method provided above, at step c), the sample or the mixture of sample and analyte ligand is subsequently exposed to sedimentation by centrifugation and gravitation (e.g., sequentially, in any order) in the reaction medium 106.

By "a) a device is provided", it is meant herein that the disclosed method is carried out using said device.

In a particular embodiment, said device is "provided" at step a) by adding reagents comprising a separation matrix 108 to the reaction medium 106 of the device 100.

Alternatively, or cumulatively, in a particular embodiment, said device is "provided" at step a) by adding reagents comprising an analyte ligand into the reaction chamber 104 and/or into the reaction medium 106.

Alternatively, or cumulatively, in a particular embodiment, said device is "provided" at step a) by adding a low-density immiscible compound 102 into the device 100.

In an embodiment, a method for detecting an analyte in a sample includes:

(a) providing a device 100 comprising a reaction chamber 104 configured to receive the sample to be tested; a separation matrix 108; and a layer composed of a low-density immiscible compound 102 that separates the reaction chamber 104 from the separation matrix 108, wherein the reaction chamber 104 is located above the separation matrix 108 within the device 100;

(b) dispensing the sample to be tested into the reaction chamber 104 of the device 100; and (c) exposing the device 100 to sedimentation by gravitation and/or centrifugation, wherein reagents comprising an analyte ligand are provided at least at step (a) and/or at step (b), and wherein if an analyte-ligand complex is formed, such mixture lies on or within the separation matrix 108 and in the absence of such complex, the mixture lies beneath the separation matrix 108, the entire reaction being carried out in the device 100.

In a particular embodiment, the device, method or use as described herein, enable detecting an analyte (for example an antibody or an antigen) in a sample by optically making visible analyte/ligand complexes (for example antigen/antibody complexes) in the device.

By "optically" is meant either detection by optical density or by image reading.

In particular, the method disclosed herein is for:

preventing the evaporation of the reagents of the reaction medium 106, in particular the evaporation of supernatant 110 in the microtube 100 of gel cards; and/or preventing the neutralization and/or consumption of the reagents (e.g., antibodies or antigens) of the reaction chamber 104 and/or of the reaction medium 106 which can give a false negative or incorrect result; and/or does not interact/interfere with the sample (e.g., red blood cells, antibodies) and reagents (e.g., antibodies) used in the test; and/or enhancing the reactivity of positive reaction without altering the specificity; and/or facilitating the distribution of the reagents (if any in the reaction chamber 104) and the sample to be tested into the device 100, in particular allowing the dispense of the reagents and the samples to be tested anywhere in the reaction chamber 104; and/or confining, before the analytical process, the reagents of the reaction medium 106 within the reaction medium 106 and especially at the bottom part of the reaction medium 106 (which may be the bottom part of the device 100) and prevents them from spreading into the reaction chamber 104 in case of shocks or reversal; and/or allowing, during the analytical process, the passage of the reagents (if any in the reaction chamber 104) and of the sample to be tested from the reaction chamber 104 through the reaction medium 106 (which may lie at the bottom part of the device 100); and/or confining, after the analytical process, all the reagents and the sample to be tested in the reaction medium 106.

Also disclosed is the use of a layer composed of a low-density immiscible compound 102 in a device 100 for detecting an analyte in a sample and especially for detecting analyte/ligand reactions (for example antigen/antibody reactions) wherein said device 100 comprises:

a reaction chamber 104 able to receive the sample to be tested (which may comprise for example antibodies or antigens); and a reaction medium 106 comprising reagents, said reagents comprising a separation matrix 108;

wherein the reaction chamber 104 lies above the reaction medium 106 within the device 100 and wherein the reaction chamber 104 and/or the reaction medium 106 optionally comprise reagents, said reagents comprising an analyte ligand; for:

preventing the evaporation of the reagents of the reaction medium 106, in particular the evaporation of supernatant in the microtube 100 of gel cards; and/or preventing the neutralization and/or consumption of the reagents (e.g., antibodies or antigens) of the reaction chamber 104 and/or of the reaction medium 106 which can give a false negative or incorrect result; and/or does not interact/interfere with the sample (e.g., red blood cells, antibodies) and reagents (e.g., antibodies) used in the test; and/or enhancing the reactivity of a positive reaction without altering the specificity; and/or facilitating the distribution of the reagents and the sample to be tested into the device, in particular allowing the dispense of the reagents (if any in the reaction chamber 104) and the samples to be tested anywhere in the reaction chamber 104; and/or confining, before the analytical process, the reagents of the reaction medium 106 within the reaction medium 106 and especially at the bottom part of the reaction medium 106 (which may be the bottom part of the device 100) and prevents them from spreading into the reaction chamber 104 in case of shocks or reversal; and/or allowing, during the analytical process, the passage of the reagents (if any in the reaction chamber 104) and of the sample to be tested from the reaction chamber 104 through the reaction medium 106 (which may lie at the bottom part of the device 100); and/or confining, after the analytical process, all the reagents and the sample to be tested in the reaction medium 106.

By "device for detecting" (or "kit for detecting") an analyte or analyte/ligand reactions, it is meant herein a device (or a kit, respectively) appropriate for use for detecting an analyte or analyte/ligand reactions respectively. In a particular embodiment, by "device for detecting" (or "kit for detecting") an analyte or analyte/ligand reactions, it is meant herein a device (or a kit, respectively) used for detecting an analyte or analyte/ligand reactions respectively.

In particular, the device disclosed herein is appropriate for use in the method disclosed herein.

By "a" or "an" (for example "an analyte" or "an analyte ligand"), it is meant herein at least one, i.e., one or several (for example one or several analyte(s) or one or several analyte ligand(s) respectively).

By "several", it is meant herein two, three, four, five or more than five.

By "detecting analyte/ligand reactions", it is meant herein detecting the formation of an analyte/ligand complex, for example using a method as disclosed herein.

Figure 2:
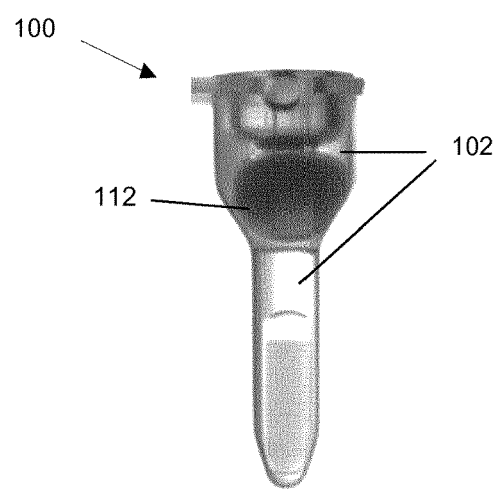
FIG. 2 illustrates a device having a low-density immiscible compound layer according to another embodiment. The low-density immiscible compound layer encapsulates a reagent and/or a sample.

In a particular embodiment illustrated in FIG. 2, the reaction chamber 104 in the device, method, or use disclosed herein comprises reagents (also referred to as the reactive medium 112), said reagents comprising an analyte ligand, and further comprises a layer composed of a low-density immiscible compound 102 as disclosed herein, which layer lies on top of said reagents, and separates said reagents, or any reagent present in the reaction chamber 104, from air. Hence, in this embodiment, the device 100 as disclosed herein contains at least two layers of a low-density immiscible compound 102, one which separates the reaction chamber 104 from the reaction medium 106, and one which separates (or insulates) the reagents comprising an analyte ligand present in the reaction chamber 104 (or any reagent present in the reaction chamber 104) from air. Said at least two layers may have identical or distinct compositions. In an embodiment, a low-density immiscible compound 102 as disclosed herein encapsulates the reagent in the reaction chamber 104.

By low-density immiscible compound 102 is meant a compound which does not mix (and especially which is totally or essentially insoluble with, or which is not able to form an homogeneous solution with) the compounds or mixtures of compounds present in the reaction chamber 104 and in the reaction medium 106, and thus remains in the device 100 as a separate compound enabling to separate the reaction chamber 104 from the reaction medium 106 (e.g., separation matrix or gel 108) and/or to separate (or insulate) reagents comprising an analyte ligand present in the reaction chamber 104 (or any reagent present in the reaction chamber 104) from air. In particular, said low-density immiscible compound 102 of the device 100, method or use as disclosed herein, has a lower density than the density of the reaction chamber 104 and a lower density than the density of the reaction medium 106.

In a particular embodiment illustrated in FIG. 1, the low-density immiscible compound 102 that separates the reaction medium 106 from the reaction chamber 104 in the device 100, method or use as disclosed herein further enables separation (or insulation) of the reaction medium 106 from air.

By "a lower density than the density of the reaction chamber" is meant that the density of the low-density immiscible compound 102 of the device 100, method or use as disclosed herein is lower than the total density of the reaction chamber 104 i.e. the sum of all the densities of the reagents of said reaction chamber 104 (if it comprises any reagents) which may include analyte ligands (for example antigens and/or antibodies), together with the density of the sample to be tested which can comprise analytes (for examples antibodies and/or antigens).

The mixture of reagents and sample in the reaction chamber 104 is referred to as the reactive medium 112 (see FIG. 2 and Example 6).

In one embodiment, the low-density immiscible compound 102 encapsulates the reactive medium 112 (e.g., the reagent and/or the sample).

By "a lower density than the density of the reaction medium" is meant that the density of the low-density immiscible compound 102 of the device 100, method or use as disclosed herein is lower than the total density of the reaction medium 106 i.e. the sum of all the densities of the reagents of said reaction medium 106 (including the density of the separation matrix 108), together with the density of the reagents comprising an analyte ligand present within the reaction medium 106, if any, and the density of any additional compound present within the reaction medium 106 (for example antibodies and/or antigens), if any.

In one embodiment, the device 100, method, or use are as disclosed herein and said low-density immiscible compound 102 has a lower density than the density of the reaction chamber 104 and a lower density than the density of the reaction medium 106.

In a particular embodiment, by "immiscible", it is meant herein immiscible in an aqueous or polar solvent (for example, water), and especially totally or essentially insoluble in said solvent. In some embodiments, the low-density immiscible compound 102 of the device, method or use as disclosed herein is hydrophobic. In a particular embodiment, the low-density immiscible compound 102 as disclosed herein has a density of less than 1, more particularly less to 0.9, 0.8 or 0.7. In particular, such density is comprised between 0.7 and 0.9, more particularly between 0.76 and 0.88.

The density of a substance is the ratio between the volumetric mass of said substance and the volumetric mass of water, said masses being measured in the same conditions of pressure and temperature. This parameter is very well known by one skilled in the art.

In one embodiment, said low-density immiscible compound 102 in the disclosed device, method, or use has a density of less than 1.

In one embodiment, the low-density immiscible compound 102 as disclosed herein is not air and thus the low-density immiscible compound 102 in the disclosed device, method or use is not air.

Still particularly, the low-density immiscible compound 102 as disclosed herein can be oil or an alkane-based compound. It can be chosen from: synthetic oil, organic oil, mineral oil, paraffin oil, paraffin such as liquid paraffin, non-polar solvents, fatty acids, for example stearic acid, alkanes mixture and pure alkane such as decane, undecane, dodecane, tridecane, tetradecane, pentadecane, hexadecane, heptadecane, octadecane, nonadacane, eicosane or heneicosane.

In a particular embodiment, the low-density immiscible compound 102 as disclosed herein is provided in the form of a composition (or low-density immiscible composition), for example a solution. Said composition can comprise one or several oil or an alkane-based compounds or mixtures thereof. For example, said composition can comprise one or several compounds chosen from: synthetic oil, organic oil, mineral oil, paraffin oil, paraffin such as liquid paraffin, non-polar solvents, fatty acids, for example stearic acid, alkanes mixture and pure alkane such as decane, undecane, dodecane, tridecane, tetradecane, pentadecane, hexadecane, heptadecane, octadecane, nonadacane, eicosane or heneicosane.

In a particular embodiment, said low-density immiscible composition further comprises one or several components chosen from metallic ions, phosphate, and viscosifiers (for example polyethylene glycol; PEG).

In a particular embodiment, the low-density immiscible compound 102 is provided in the form of a composition comprising or consisting of gelled hydrocarbons.

By "organic oil", is meant animal or vegetable oil such as for example peanut oil, rapeseed oil or castor oil.

By "synthetic oil", it is meant any oil consisting of chemical compounds that are artificially made (synthesized). An example of synthetic oil can be silicone oil.

Mineral oil can be defined as a mixture of hydrocarbons, essentially paraffinic and naphthenic in nature obtained from petroleum, for example a mixture of alkanes between C15 and C40. Examples of mineral oil can be naphthenic oil or paraffinic oil.

Examples of non-polar solvents oil can be cyclodecane.

Alkanes are saturated hydrocarbons which consist only of hydrogen and carbon atoms ($C_nH_{2n+2}$) linked by single bonds. Alkanes are non-polar molecule which do not form hydrogen bonds and consequently are insoluble in polar solvents such as water.

Examples of alkanes as disclosed herein are further described in Table 1 below.

TABLE 1

| Name | Tetradecane | Pentadecane | Hexadecane | Heptadecane | Octadecane | Nonadecane |
|---|---|---|---|---|---|---|
| Molecular Formula | $C_{14}H_{30}$ | $C_{15}H_{32}$ | $C_{16}H_{34}$ | $C_{17}H_{36}$ | $C_{18}H_{38}$ | $C_{19}H_{40}$ |
| Linear Formula | $CH_3(CH_2)_{12}CH_3$ | $CH_3(CH_2)_{13}CH_3$ | $CH_3(CH_2)_{14}CH_3$ | $CH_3(CH_2)_{15}CH_3$ | $CH_3(CH_2)_{16}CH_3$ | $CH_3(CH_2)_{17}CH_3$ |
| Source | Mineral source (distillate of petroleum) | | | | | |
| Melting point (° C.) | ~5.5 | 8-10 | 17.5-18.5 | 20-22 | 26-29 | 30-34 |
| Density | 0.762 | 0.769 | 0.773 | 0.777 | 0.777 | 0.786 |

In one embodiment, said low-density immiscible compound 102 in the disclosed device, method, or use, is chosen from or is provided in the form of a composition comprising one or several compounds chosen from: synthetic oil, aromatic oil, organic oil, naphthenic oil, mineral oil, paraffinic oil, paraffin such as liquid paraffin, non-polar solvents, alkanes mixture and pure alkane such as decane, undecane, dodecane, tridecane, tetradecane, pentadecane, hexadecane, heptadecane, octadecane or nonadecane.

Still particularly, the low-density immiscible compound 102 can be solid or liquid at room temperature. One skilled in the art is able to determine what is encompassed by "room temperature". In a particular embodiment, it is meant a temperature comprised between 18 and 25° C.

In one embodiment, the low-density immiscible compound 102 in the disclosed device, method, or use is liquid at room temperature (for example between 18 and 25° C.).

It can be for example made of a mixture of alkanes where the alkanes are between C15 and C40 (C referring to the number of carbon atoms in the alkane), or made of pure alkanes from C15 to C17.

It can also be for example made of pure alkanes where the alkanes are between C15 and C40, C15 to C20, C16 to C20, C17 to C20 or C18 to C19.

It can also be for example made of a mixture of alkanes where the alkanes are between C15 to C20, C16 to C20, C17 to C20 or C18 to C19.

It can also be for example made of a mixture of alkanes between C15 and C40 with a density between 0.82 and 0.88, for example a mixture of alkanes between C15 to C20, C16 to C20, C17 to C20 or C18 to C19 with a density between 0.82 and 0.88.

In one embodiment, the low-density immiscible compound 102 in the disclosed device, method, or use is solid at room temperature (for example between 18 and 25° C.).

It can also be for example made of pure alkanes with C number higher than 18.

In case of a solid low-density immiscible compound 102 at room temperature (for example between 18 and 25° C.), said solid compound can be further liquefied thermally, chemically or physically.

Hence, in one embodiment, the solid compound in the disclosed device, method, or use can be further liquefied, thermally, chemically or physically.

The solid compound can for example by liquefied physically by ultrasound.

The solid compound can for example be liquefied thermally by elevating the temperature, for example when, during the test to be carried out, the device is incubated at 37° C. In this example, the compound becomes liquid temporarily, during the reaction, but it again becomes solid when the reaction is completed and when the device is put back to room temperature.

Octadecane ($C_{18}H_{38}$) and nonadecane ($C_{19}H_{40}$) can be cited for example.

The solid compound can also for example be liquefied chemically by adding just before the test is carried out, another compound which decreases the melting temperature of the solid compound below room temperature and consequently liquefies the solid compound for example at room temperature (in particular between 18 and 25° C.).

Melting temperature of alkanes is correlated with C number. By mixing different pure alkanes with different melting temperature, it is possible to set precisely the melting temperature at +/−1° C. in order to obtain a solid low-density immiscible compound at room temperature which becomes liquid after 37° C. incubation.

For example, addition of decane ($C_{10}H_{22}$) (melting temperature=−30° C.) to octadecane (melting temperature=29° C.) decreases the melting temperature of the mixture octadecane/decane below room temperature and consequently liquefies the alkane layer.

As such, a thermic melting can be considered for example for applications involving incubations such as Indirect Antiglobulin Test or antibody screening and a chemical melting can be considered for application carried out at room temperature such as Direct Antiglobulin Test, grouping, phenotyping, etc.

Other applications and advantages are, for example, the control of incubation as well as the control of the storage temperature of the device. Indeed, by the change of aspect of the solid low-density immiscible compound 102 as disclosed herein from a solid state to a liquid state, it is possible to control that the incubation is taking place and to control the temperature. Alternately, for devices that have to be stored at for example 2-8° C., the change of the solid low-density immiscible compound from a solid state to a liquid state, after the reaction has been carried out, is an indication that the reagents have reached room temperature.

The quantity of low-density immiscible compound 102 as disclosed herein is sufficient to cover the reaction medium and thus separates the reaction medium from the reaction chamber entirely. Such quantity will thus be variable depending on the specific device. For example, it can be between 150 and 200 µL. It can also be at least 3 µL preferably from 5 to 50 µL especially when the device is a gel card.

As previously mentioned, the disclosed device comprises a reaction chamber 102 and a reaction medium 106. In a particular embodiment, by "the reaction chamber 104 lies above the reaction medium 106", it is meant herein that the reaction chamber 104 is at the top part of the device 100 and the reaction medium 106 is at the bottom part of the device 100.

The reaction chamber 104 is able to receive the sample to be tested and may comprise or receive reagents, said reagents comprising an analyte ligand. A sample to be tested is preferably a biological sample, which can be diluted using any appropriate buffer and/or diluent.

For example, said sample can comprise or consist of a biological fluid, and especially of blood (for example whole blood), a blood derivative (for example plasma or serum) or urine, cerebrospinal fluid, saliva or cells (for example erythrocytes), or mixtures thereof.

In a particular embodiment, a sample to be tested comprises or consists of whole blood, serum, plasma and/or erythrocytes (also called red blood cells).

An analyte to be detected in a sample can be any type of compound, natural, recombinant or synthetic. It can be for example a protein (for example a native protein, a fragment thereof or a recombinant protein), a peptide (for example, a synthetic peptide), a glycoprotein, a glucide, a lipid, a cell, an organite, a virus or a nucleic acid.

An analyte to be detected in a sample can be for example a bacterium, a fungi, a yeast or a parasite.

An analyte to be detected in a sample can be for example chosen from the group consisting of an antigen, an antibody, a hapten, a hormone, a hormone receptor, an enzyme, and fragments thereof.

In a particular embodiment, the analyte(s) to be detected are not nucleic acids.

In a particular embodiment, the analyte(s) to be detected are or include antibodies and/or antigens.

In a particular embodiment, the device, method and use described herein are for detecting antibody-antigen reactions.

In a particular embodiment, an analyte to be detected (for example antibodies and/or antigens) can be bound to a carrier in a sample, and especially bound to cells, for example erythrocytes.

By "analyte ligand" (or "ligand"), it is meant herein any compound able to bind to an analyte to be detected, for example antigens and/or antibodies.

In a particular embodiment, said analyte ligand specifically binds to an analyte to be detected.

By "antigen", it is means herein a natural, recombinant or synthetic antigen. Said antigen can be for example a protein (for example a native protein, a fragment thereof or a recombinant protein), a peptide (for example, a synthetic peptide), a glycoprotein, a glucide or a lipid, or a fragment thereof.

By "antibody", it is meant herein a monoclonal antibody or a polyclonal antibody, or a fragment thereof.

In a particular embodiment, said antibody is specifically directed against (i.e., specifically binds to) an analyte to be detected in a sample.

In a particular embodiment, said antibody is directed against, and especially specifically directed against (i.e., specifically binds to) blood group antigens, for example ABO blood group antigens.

In a particular embodiment, the analyte ligand or one of the analyte ligands is an immunoglobulin or a mimotope, which is used as antigen and/or antibody.

In a particular embodiment, the analyte ligand(s) used as described herein are not nucleic acids.

In a particular embodiment, one or several of the analyte ligands (for example antibodies and/or antigens) used as described herein are bound to a carrier (as described herein), and especially bound to cells, for example erythrocytes.

The reaction medium 106, which may lie for example at the bottom part of the device, comprises reagents.

Said reagents comprise a separation matrix 108. In a particular embodiment, the reaction medium 106 further comprises reagents, said reagents comprising an analyte ligand.

In a particular embodiment, said reaction medium 106 also comprises additional compounds, for example one or several antibodies (especially anti-human antibodies, e.g., anti-human globulin (AHG)) and/or antigens. In one embodiment, the reaction medium 106 of the disclosed device, method, or use comprises reagents, said reagents comprising a separation matrix 108 and one or several antibodies and/or antigens.

Devices for detecting analyte/ligand reactions and especially antigen/antibody reactions, without the low-density immiscible compound 102 as disclosed herein are well known to one skilled in the art and are commercially available.

Such kind of devices is described in the patent U.S. Pat. Nos. 5,460,940, 5,512,432 or EP0305337, from which the content is incorporated by reference.

In one embodiment, the carrier to which an analyte ligand is bounded is colored or tagged, for example by color, isotope, fluorescence or enzyme.

A carrier can consist of cells such as erythrocytes, leukocytes, or platelets or bio-particles such as cells-derived vesicles, cellular microparticles, virus like particles or liposomes or synthetic particles such as latex or gold beads.

The separation matrix 108 (and thus, the reaction medium 106) as described herein can be any matrix that provides a sieving effect in such a way that upon the action of gravitational forces and/or centrifugal forces as disclosed herein, the sample or the mixture of sample and analyte ligand will either (i) be retained on or within the separation matrix 108 if an analyte/ligand complex is formed or (ii) sediment beneath the separation matrix 108 in the absence of such complex.

The separation matrix 108 is preferably an inert matrix, more preferably an inert particulate matrix. The term "inert" is intended to mean that the matrix must not enter into any unspecific reactions with an analyte to be detected or an analyte ligand.

Inert porous particles as commercially available for liquid or gas chromatography or for gel cards can be used. Porous glass or silica gel also enters into consideration. Those skilled in the art can determine by means of simple preliminary experiments whether particles can be used as separation matrix 108 as disclosed herein.

The separation matrix 108 as described herein can be a slurry or a suspension or a mesh of particles or any solid network such as, for example, cellulose. The separation matrix 108 of the device 100 can be, for example, polymers of acrylamide, or dextran or glass microparticles (for example glass beads).

Antibodies used as analyte ligands (for example to detect antigens) can be directed against carbohydrates, proteins from blood cells (for example blood group antigens), viruses, bacteria, fungi, yeasts, parasites.

Antigens used as analyte ligands (for example to detect antibodies) can be components of body fluid such as blood, serum or plasma, for example blood group antigens and especially ABO blood group antigens, or fragments thereof, or recombinant proteins derived thereof.

Still particularly, in one embodiment of the method, the low-density immiscible compound 102 covering the reaction medium 106 (e.g., the separation matrix 108) eliminates the need to maintain an air gap between the low-density immiscible compound 102, the reagents, and the sample in the reaction chamber 104 when the sample and reagents are added to the device 100.

In one embodiment, the device 100 as disclosed herein does not comprise any air gap between the reaction chamber 104 and the reaction medium 106, especially when using the device 100 in the disclosed method. More particularly, it does not comprise any air gap between the low-density immiscible compound 102 and the reaction medium 106, especially when using the device 100 in the disclosed method.

In one embodiment, the device 100 of the disclosed device, method, or use does not comprise any air gap between the reaction chamber 104 and the reaction medium 106.

In a particular embodiment, the device 100 of the disclosed device, method, or use does not comprise any air gap between the low-density immiscible compound 102 and the reaction medium 106.

It provides a particular advantage when compared to the devices of the prior art, wherein said air gap is technically difficult to implement and it thus results in an improvement of the robustness of the device as disclosed herein.

As already mentioned, devices for detecting an analyte in a sample and especially devices for detecting analyte/ligand reactions are well known in the art. It can be for example an immunoassay such as microplate containing microtubes such as 96, 392 or 1536 wells, a Column Agglutination Technology device, for example a gel card and in particular a gel blood typing card, or a particle gel immunoassay (e.g., a PaGIA or an ID-PaGIA) test device.

In one embodiment, the disclosed device is thus an immunoassay such as microplate containing microtubes such as 96, 392 or 1536 wells, a Column Agglutination Technology device, for example a gel card and in particular a gel blood typing card, or an ID-PaGIA test device.

As a consequence, in a particular embodiment, the use of the low-density immiscible compound 102 as disclosed herein allows the optimization of diagnostic or immuno-diagnostic devices (including the immuno-hematology analysis devices), in particular gel cards.

Additionally, the low-density immiscible compound 102 prevents "neutralization phenomenon" in tests involving Anti-Human Globulin.

Neutralization phenomenon refers herein to the interaction of reagents with Anti-Human Globulin, resulting in a false negative result or an incorrect result (see Example 3).

The low-density immiscible compound 102 also facilitates the manual/automated dispensing of small volumes (for example 10 to 100 µL) in microtubes (see Example 6). In particular, the low-density immiscible compound 102 allows the dispensing of the reagents and the samples to be tested anywhere in the reaction chamber 104 or even anywhere in the low-density immiscible compound 102, which greatly simplifies the dispense operations.

In addition, when the low-density immiscible compound 102 as disclosed herein is in solid form at room temperature (e.g., 18-25° C.), said compound forms a type of cap in microtubes. At the beginning of the test, the compound is liquefied by bringing the device to the compound's melting point, allowing samples added to the microtubes 100 (e.g. samples of red blood cells) to make contact with the gel in the microtubes 100 during the test. After the reaction (particularly after centrifugation), the compound can be allowed to re-solidify, so as to secure the gel card used for the test (this is useful in the case where the gel card used must be preserved and not discarded after the test). The melting of the low-density immiscible compound 102 may be done, for example, through a heating zone located at the platform to perform the centrifugation.

Alternately, the solid compound can be liquefied without temperature elevation, for example by using two compounds of weak immiscible density: a first compound that is solid at room temperature, with a melting point that is, for example around 30-34° C., which serves as a plug in the microtubes, and a $2^{nd}$ compound, liquid at room temperature, having a melting point such that when poured into the first compound, it liquefies.

As a consequence, the low-density immiscible compound 102 as disclosed herein secures, before analytical process, the transportation of gel cards by confining reagents into microtubes (reaction medium 106) and thus, preventing exit of reagents from microtube 100 to reaction chamber 104.

Finally, the low-density immiscible compound 102 secures, after analytical process, cards by confining reagent or samples in the reaction chamber 104, preventing exposure of user to contaminants.

In one embodiment, the device disclosed herein is a gel card characterized in that one or several microtubes 100 of said gel card comprise(s) a layer composed of a low-density immiscible compound 102 as disclosed herein, which lies above the reaction medium 106 (i.e., above the gel 108 and the supernatant 110) in said microtube(s). Said device 100 can be used to implement the method disclosed herein.

Different types of analyte/ligand reactions can be detected by the device 100 as disclosed herein. It can be for example, immunohematology analyte/ligand reactions, especially immunohematology antigen/antibody reactions, in particular tests using Anti-Human Globulin such as Direct Antiglobulin Test or Indirect Antiglobulin Test, or tests such as ABO forward and reverse typing. All these examples are well known by one of ordinary skill in the art.

In one embodiment, the analyte/ligand reactions, especially the antigen/antibody reactions are thus immunohematology antigen/antibody reactions, in particular tests using Anti-Human Globulin, or tests such as ABO forward and reverse typing.

In addition to all the previously mentioned advantages of the low-density immiscible compound 102 as disclosed herein, the inventors have further shown that said compound improves the reactivity between analytes and ligands and especially between antigens and antibodies. See Example 5.

As a summary, the low-density immiscible compound 102 according to the invention allows:

prevention of evaporation, gel drying: increase of shelf life, increase of stability after opening/piercing: improve "well by well" management on instrument, reduction of sealing constraints to reduce costs, reduction of foil solidity to implement needle piercing and facilitate manual opening, delayed reading;

Increase of robustness versus air gap: increase throughput by removing air gap checking step;

reactivity enhancement: performances improvement;

prevention of transport deterioration: especially reduction of contamination risk at opening/piercing;

confining reagents and samples within the reaction medium 106; securing the device 100 after processing, encapsulation of reagents (pre-dispensed reagent);

depending on the device: facilitation of dispense: reduction of dispense constraints: increase of dispense speed to increase throughput, control of dispensed volume.

In one embodiment, it is further provided a kit for detecting an analyte in a sample, and especially for detecting analyte/ligand reactions (in particular antigen/antibody reactions), said kit comprising a device as disclosed herein and, optionally, a package insert.

In another embodiment, a kit is provided for detecting an analyte in a sample, and especially for detecting analyte/ligand reactions, which comprises:
- a device 100 comprising a reaction chamber 104 able to receive the sample to be tested, and a reaction medium 106 comprising reagents, said reagents comprising a separation matrix 108, wherein the reaction chamber 104 lies above the reaction medium 106 within the device 100, and wherein optionally, the reaction chamber 104 and/or the reaction medium 106 comprise reagents, said reagents comprising an analyte ligand, as described herein;
- a low-density immiscible compound 102 as described herein;
- optionally, reagents comprising an analyte ligand; and
- optionally, antibodies and/or antigens.

In a further embodiment, a kit is provided for detecting an analyte in a sample, and especially for detecting analyte/ligand reactions, said kit comprising:
- a device 100 comprising a reaction medium 106 and a reaction chamber 104, as described herein, which reaction chamber 104 lies above the reaction medium 106 within the device 100, wherein, optionally, the reaction chamber 104 and/or the reaction medium 106 comprise reagents, said reagents comprising an analyte ligand, as described herein;
- reagents comprising a separation matrix 108;
- a low-density immiscible compound 102 as described herein;
- optionally reagents comprising an analyte ligand; and
- optionally antibodies and/or antigens.

The kits disclosed herein can be used to implement the method disclosed herein.

The disclosed device, method, use and kit will be further illustrated by the following examples.

EXAMPLES

Example 1

Test of Biocompatibility

The objective of this experiment was to show the compatibility of a low-density immiscible compound 102 as disclosed herein with biological components (erythrocytes, antibodies, buffer . . . ) in Indirect Antiglobulin Test.

Method

Two samples (weak monoclonal antibody anti-RH4 for positive and serum or plasma with no anti-RBC antibody for negative) were tested in Indirect Antiglobulin Test on Anti-IgG card against a pool of frozen R1r cells diluted at 1% in ID-Diluent 2:
- without oil: Ctrl (=control);
- with 5 µL oil (white mineral oil; CAS #8042-47-5);
- with 10 µL oil (white mineral oil; CAS #8042-47-5).

Results

The results are presented in FIG. 3.

In the microtube containing mineral oil, neither significant difference of reactivity nor hemolysis was observed compared to Ctrl microtube for both positive and negative samples. Due to its immiscible characteristic, mineral oil did not interact with supernatant (e.g., reagent containing antibodies), red cells (e.g., the red blood cell membrane phospholipid bilayer) and samples which all contain an aqueous base. Thus, no significant interaction was observed between the mineral oil and the reagent or samples as compared to Ctrl.

Example 2

Test of Evaporation

The objective of this experiment was to show the capability of a low-density immiscible compound 102 as disclosed herein to prevent evaporation of the supernatant and drying of the gel.

Method

Three µL, 4 µL, 5 µL and 10 µL of oil (white mineral oil; CAS #8042-47-5) were added in microtubes of an Anti-IgG card. This card was stored opened at 56° C. Loss of supernatant was visually estimated in comparison to Ctrl well (no oil) using the grades described in the following Table 2.

TABLE 2

| Observed effects | Grade |
| --- | --- |
| No evaporation of supernatant, no drying of gel | − |
| Partial evaporation of supernatant, no drying of gel | + |
| Total evaporation of supernatant, no drying of gel | ++ |
| Total evaporation of supernatant, partial drying of gel | +++ |
| Total evaporation of supernatant, total drying of gel | ++++ |

Results

The results are presented in FIG. 4.

In the control well, the supernatant was totally evaporated and gel was entirely dried after 4 h-storage of unsealed card at 56° C. Neither supernatant evaporation nor gel drying was observed with 3, 4, 5 and 10 µL of low-density immiscible compound as disclosed herein. By preventing supernatant evaporation, low-density immiscible compound as disclosed herein could be used to increase real time stability of card and on-board stability on instruments. By preventing evaporation, low-density immiscible compound as disclosed herein avoids condensation and reduces the risk of contamination at opening/piercing due to droplets of supernatant on aluminum foil of card and/or the hemolysis of RBCs by condensation droplets. Use of low-density immiscible compound 102 as disclosed herein could reduce industrial constraints in the sealing of the device during the manufacture of the gel card. Because the L-DIC 102 prevents evaporation, the thickness of the foil used to seal the device could be reduced and the amount of glue needed to attach the foil to the device could be reduced.

Example 3

Test of Neutralization-Robustness to Air Gap

The objective of this experiment was to show the capability of a low-density immiscible compound 102 as disclosed herein to increase the robustness regarding air gap in Indirect Antiglobulin Test.

Method

A weak anti-RH4 was tested in Indirect Antiglobulin Test on the ID-Card LISS/COOMBS (Anti-IgG/-C3d) against R1r cells according to the product's Indications For Use:
- without oil (Ctrl) and with 5 μL oil (white mineral oil; CAS #8042-47-5); and
- with and without air gap.

Results

The results are presented in FIG. 5.

In the absence of air gap, weak anti-RH4 was consumed by Anti-Human Globulin during incubation at 37° C. inducing a negative reaction instead of 2+ reaction (Ctrl). In the absence of air gap, but with 5 μL oil, reactivity of weak anti-RH4 antibody remained 2+ as expected. By isolating reactive medium from AHG, oil prevents antibody (reagent) consumption by AHG during incubation. In addition, oil increases the reactivity of the top-part of the gel.

The low-density immiscible compound 102 as disclosed herein increased the robustness by making optional the airgap during the Indirect Antiglobulin Test. Use of L-DIC will also allow inverse dispensing (dispense plasma into the reaction chamber before erythrocytes). Without L-DIC, AHG neutralization is typically greater when the plasma is dispensed into the reaction chamber before erythrocytes.

Example 4

Test of Integrity of Gel/Supernatant

The objective of this experiment was to show the capability of a low-density immiscible compound 102 as disclosed herein to increase the robustness regarding transportation.

Method

Cards containing gel and supernatant were filled with solid or liquid low-density immiscible compound 102 as disclosed herein (5 μL of octadecane (CAS #: 593-45-3) and 5 μL of white mineral oil (CAS #8042-47-5) respectively) and compared to Ctrl well (no low-density immiscible compound as disclosed herein added).

Produced cards were manually shaken in order to simulate transport conditions (until total destructuration of Ctrl well).

Cards were then centrifuged in ID-Centrifuge (Bio-Rad Laboratories) and the re-organization capability of cards was studied visually.

Results

The results are presented in FIG. 6.

After manual shaking to simulate transport conditions, Ctrl microtubes were not reorganized correctly after centrifugation (presence of bubbles, gel still in the top-part of microtube, . . . ) whereas gels with solid or liquid low-density immiscible compound as disclosed herein became less destructured after shaking and consequently were correctly re-organized after centrifugation making back the device suitable for use.

As a consequence, it was showed that the low-density immiscible compound 102 according as disclosed herein mitigates card deterioration and increase robustness regarding transportation.

Example 5

Reactivity Enhancement Without Specificity Degradation

The objective of this experiment was to show the capability of a low-density immiscible compound 102 as disclosed herein to increase reactivity without degrading specificity on ABD performances with A weak and O donors' samples.

Method

"DiaClon ABD-Confirmation card for Patient" ID-Cards were modified according to the following protocol:
"REF": no oil added in microtubes 1, 2 and 3.
"Oil": add 5 μL of oil (white mineral oil; CAS #8042-47-5) in microtubes 4, 5 and 6.
Centrifuge card in ID-Centrifuge (Bio-Rad Laboratories) before proceeding as mentioned in Table 3.

TABLE 3

| A | B | D | A | B | D |
|---|---|---|---|---|---|
| REF | REF | REF | +5 μL oil | +5 μL oil | +5 μL oil |

12 A weak samples and 20 EDTA donor Group O samples were tested on these cards as follows:
Dilute 25 μL of packed RBC in 500 μl of ID-Diluent 2 (5% suspension);
Dispense 12.5 μL of 5% RBC suspension in each microtube;
Centrifuge for 10 minutes at 85 g (ID-centrifuge); and
Read and record the reaction.

Results

Figure 7:
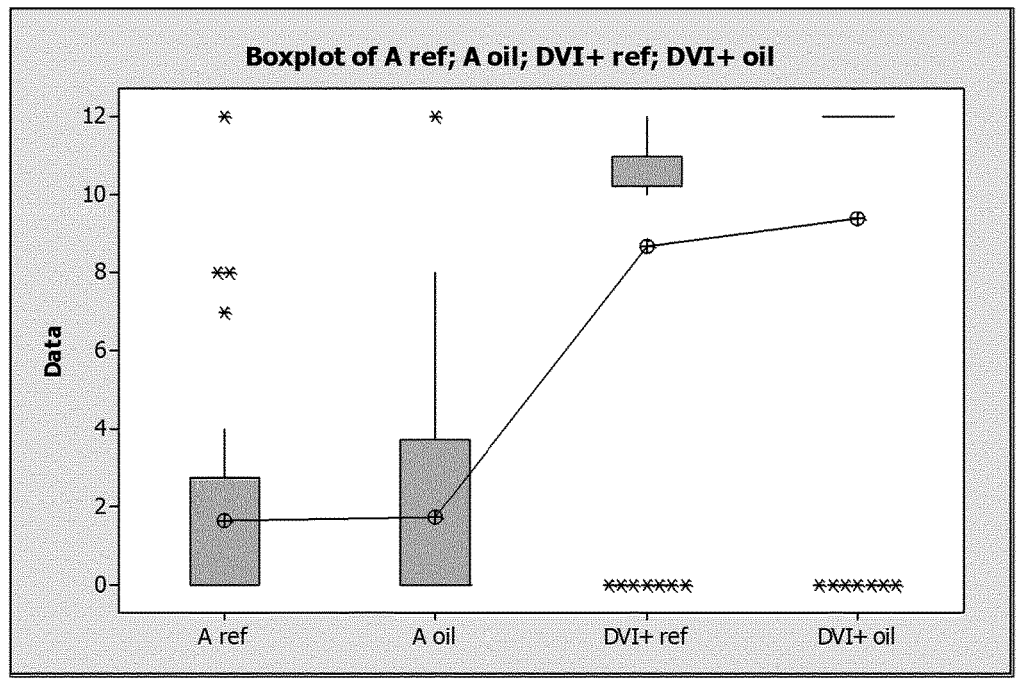
FIG. 7 illustrates the results of a test of reactivity enhancement with a low-density immiscible compound according to one embodiment (A means anti-ABO1 reagent, DVI means anti-RH1 partial category VI (DVI) reagent, both of which are used in blood typing embodiments).

The results are presented in FIG. 7.

No significant (p=0.181) difference was observed with and without oil on reactivity of weak A samples. Consequently, the layer of oil had no impact on anti-A reactivity. Nevertheless, it was observed that anti-D well to which the layer of oil had been added reacted systematically stronger. The layer of oil increased slightly but significantly (p=0.000) the DVI+ reactivity.

Additionally, oil had no impact on the specificity of the test (no unspecific reaction was observed with EDTA donors sample of Group O, n=20).

Example 6

Facilitation of Dispense

The objective was to show the capability of a low-density immiscible compound 102 as disclosed herein to facilitate the pipetting of reagents and samples into the reaction chamber 104.

Method

Production of Card

ID-Cards LISS/COOMBS cards were opened and were modified according to the following protocol:
microtubes 1 and 2: no oil added (Ctrl);
microtubes 3 and 4: 5 μL of oil (white mineral oil; CAS #8042-47-5) added; and
microtubes 5 and 6: 50 μL of oil added.

Figure 8:
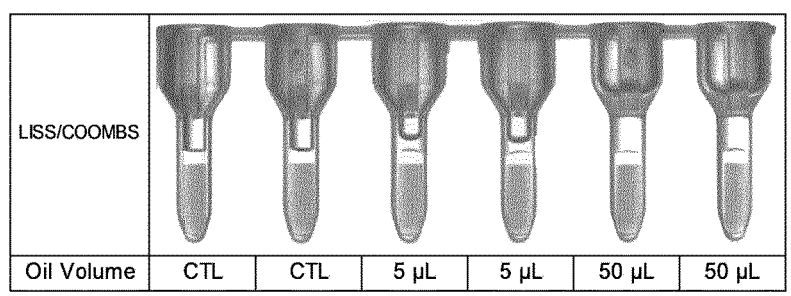
FIG. 8 illustrates the production of a card for use in a test of ease of dispensing of a low-density immiscible compound.
Figure 12:
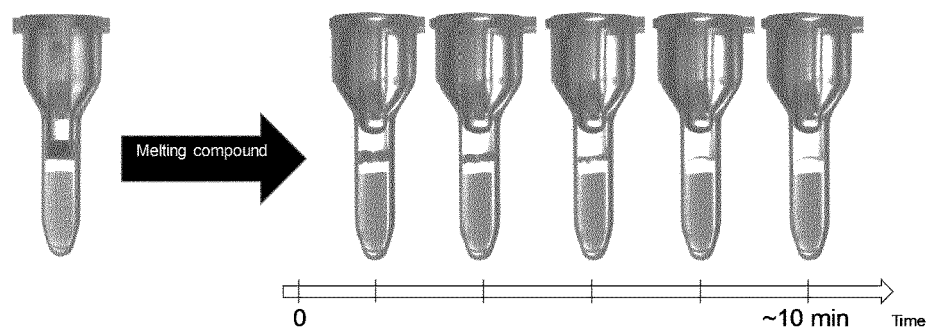
FIG. 12: illustrates the "modular cover plate" made with a low-density immiscible compound according to one embodiment which changes of state without any change of temperature.

Then, cards were centrifuged in ID-centrifuge (Bio-Rad Laboratories) (see FIG. 8).

A positive (weak anti-RH4 giving a 2+ reaction) and negative (serum or plasma from AB group with no anti-RBC antibody) samples were tested on these cards as follows:
50 μL of 1% RBC Suspension;
25 μL of positive or negative samples;
Incubate 15 min at 37° C.;

Centrifuge for 10 min at 85 g; and
Read the reaction.
Results

50 µL of 1% RBC suspension and 25 µL of sample ("the reactive medium") were trapped into oil (50 µL) just above the cylindrical part of microtube. The oil maintained the reactive medium 106 in a spherical conformation and this configuration remained stable even during moving and/or incubation of card.

The results are presented in FIG. 9.

Empirically, it was observed that 50 µL of liquid low density immiscible compound 102 facilitated low-volume dispensing into the reaction chamber. Without the low density immiscible compound 102, low volumes of reactive medium 112 will stick to the dispense tip. The human operator of the dispenser typically touches the reactive medium 112 droplet to support to add the droplet to the reaction chamber 104. When an automated dispenser is used, to prevent a small drop from adhering to the dispense tip, the dispense speed is increased and the support is ionized (e.g., ions are sprayed onto the support surface) to neutralize the repulsive charge on the support surface to release the droplet. In this example, the low density immiscible compound 102 confined the dispensed reactive medium 112 in a spherical conformation within the low density immiscible compound 102 and thus the reactive medium 112 did not adhere to the dispensing device. This property facilitates automated dispensing of low-volumes of around 10 µL and avoids having to ionize the support or having to use low speed dispensing.

By using solid low-density immiscible compound as disclosed herein, reactive medium 112 (reagent, buffer, and cell) was encapsulated within the microtube 100 to allow manufacture of "pre-dispensed" cards which remain stable during transport and/or incubation of the cards.

Example 7

Thermally Dependent Modular Cover Plate with a Low-Density Immiscible Compound as Disclosed Herein The objectives were to demonstrate the capability of a low-density immiscible compound 102 as disclosed herein to act as a "modular cover plate" (e.g., a layer that covers the microtube of the gel card) which can change state from liquid to solid or from solid to liquid depending on temperature.

Method

ID-Cards LISS/COOMBS were opened and were modified according to the following protocol:
Card 1: microtubes 1 and 2: no oil added (Ctrl)
  microtubes 3 and 4: 5 µL of white mineral oil (CAS #8042-47-5);
  microtubes 5 and 6: 5 µL of octadecane (CAS #593-45-3).
Card 2: microtubes 1 and 2: 5 µL of nonadecane (CAS #629-92-5).

Octadecane and nonadecane were pre incubated and pre heated to obtain a liquid form.

Then, cards were centrifuged in ID-centrifuge (Bio-Rad Laboratories).

A positive (weak anti-RH4 giving a 2+ reaction) and negative (serum or plasma from AB group with no anti-RBC antibody) samples were tested on these cards as follows:
50 µL of 1% RBC Suspension;
25 µL of positive or negative sample;
Incubate 15 min at 37° C.;
Centrifuge for 10 min at 85 g; and
Read the reaction.
Results The results are presented in FIGS. 10 and 11.

Negative control reacted as expected, with 5 µL white mineral oil, with 5 µL octadecane and with 5 µL nonadecane.

Weak anti-RH4 reacted as expected, with 5 µL white mineral oil, with 5 µL octadecane and with 5 µL nonadecane despite the pre incubation of the latter two.

The feasibility of a "modular cover plate" which can change state depending on temperature was demonstrated. Octadecane and nonadecane were used to seal the microtube. During the 37° C. incubation process of IAT, these components become liquid, allowing the red blood cells to be centrifuged.

Example 8

Chemically Dependent Modular Cover Plate with a Low-Density Immiscible Compound as Disclosed Herein The objective was to show the capability of a low-density immiscible compound 102 as disclosed herein to change of state without any change of temperature and consequently to show the capability of the low-density immiscible compound 102 to be used for room temperature assays such as Direct Antiglobulin Test and phenotyping.

Method

The melting temperature of octadecane (CAS #593-45-3) is: 26-29° C. and the melting temperature of decane (CAS #124-18-5) is −30° C.

A ID-Card LISS/COOMBS was filled with 5 µL of octadecane, then 5 µL of decane was added in card and card was read every minute (see FIG. 10).

The addition of decane (Tm=−30° C.) to octadecane (Tm=29° C.) decreased the melting temperature of the mixture octadecane/decane below room temperature and consequently liquefied the alkane layer.

The solid octadecane layer was liquefied in about 4 min.

Results

Test of Alkanes in DAT

3 Quality Control samples (DAT negative, IgG-sensitized and C3-sensitized RBCs) were tested on ID-Cards LISS/COOMBS in Direct Antiglobulin Test according to the product's Indications For Use:
"Ref": well without alkanes;
"5 µL octa": 5 µL octadecane in microtube;
"5 µL octa+5 µL deca": 5 µL octadecane+5 µL decane in microtube.

Different room temperature-incubation duration between dispense of decane and dispense of samples were tested:
5 min;
10 min.

The results are shown in FIG. 13.

With 5 and 10 min room temperature incubation, results with 5 µL octadecane+5 µL decane were equivalent to reference.

Tests of Alkanes in Reverse Typing

2 EDTA Donor's samples (Group AB and group O) were tested with A1, B and O red blood cell on ID-Cards NaCl, Enzymes and Cold agglutinins in reverse typing according to the product's Indications For Use:
"Ref": well without alkanes;
"5 µL octa": 5 µL octadecane in microtube;
"5 µL octa+5 µL deca": 5 µL octadecane+5 µL decane in microtube.

The room temperature incubation of 10 min necessary for the reverse typing method was used to melt the octadecane layer.

The results are shown in FIG. 14.

Results with 5 µL octadecane+5 µL decane were equivalent to reference.

As a consequence, the addition of decane (Tm=−30° C.) to octadecane (Tm=29° C.) decreased the melting temperature of the mixture octadecane/decane below room temperature and consequently liquefied the alkane layer.

Example 9

Effect of a Low-Density Immiscible Compound as Disclosed Herein on ID-HbS (Hemoglobin S) Card The objective was to evaluate the effect of a low-density immiscible compound 102 as disclosed herein on ID-HbS card (test commercially available).

Material

Reagents (see Table 4 below)

TABLE 4

| Agent Name | Lot |
|---|---|
| White mineral oil | CAS# 8042-47-5 |
| ID-Card "ID-HbS" Sickle Cell | Test 50610.10.01 |
| ID-HbS reduction agent lyophilized | 04170.57.11 |
| Dia cell I "Sickle Cell" brazil | 16113 HBS8 |
| Dia cell II "Sickle Cell" brazil | 16123 HBS8 |
| ID Diluent 2 | 05761.50.20 |

Blood Samples (see Table 5 below)

TABLE 5

| N° | Barcode |
|---|---|
| 1 | 206378502 |
| 2 | 206379303 |
| 3 | 206379402 |
| 4 | 3014086502 |
| 5 | 206375003 |
| 6 | 206381101 |
| 7 | 3014161602 |
| 8 | 206376202 |
| 9 | 206380502 |
| 10 | 3014162401 |

Instruments (see Table 6 below)

TABLE 6

| Instrument | Serial Number |
|---|---|
| ID-Reader Saxo | Bio-Rad N° 3042 |
| Leica Microscope | Bio-Rad N° 4223 |

Method

Preparation of card:

An ID-Card "ID-HbS" Sickle Cell Test was prepared by adding 5 µL of mineral oil (Sigma M8410): oil was dispensed with Multipette Eppendorf and the cards were used afterwards within 30 minutes, no centrifugation before testing.

Test on card (ID-Card "ID-HbS" Sickle Cell Test):

10 EDTA patients and 2 sickle cell positive samples were tested on:
ID-Card "ID-HbS" Sickle Cell Test without Oil ("REF")
ID-Card "ID-HbS" Sickle Cell Test with 5 µL Oil ("Oil")
The working solution was prepared by adding 10 mL of deionized water to the lyophilized reducing agent, and mixed gently until the powder is dissolved (the working solution was used within 2 h after preparation.)

For each sample: 200 µL of working solution were pipetted into a glass-tube, 10 µL of packed RBC were added immediately and mixed gently: the color changed from red to "burgundy";

The tubes were incubated for 2-10 minutes at room temperature

The cells were gently re-suspended and 20 µL pipetted into the microtubes

Centrifugation for 10 minutes at 85 g (ID-centrifuge) took place

The reaction (Saxo reader) was read and recorded

Results

The results are shown in FIG. 15.

Positive results were obtained on cards with oil which look slightly better than cards having no oil. With oil the reactions are noted at 4−, without oil at 3+, both with double population.

Negative results were similar on both cards (with- or without oil)

No false positive were due to oil.

Example 10

Effect of a Low-Density Immiscible Compound as Disclosed Herein in PaGIA Tests

The objective was to evaluate if addition of a low-density immiscible compound 102 as disclosed herein in PaGIA has an impact on performances (sensitivity and specificity) of ID-PaGIA IgA deficiency, anti-IgA antibody and Syphilis tests.

Material:

White Mineral Oil: CAS #8042-47-5

Anti IgA Test:
ID-PaGIA anti IgA Ab test KIT-ref 020601V (lot 458601701) (including positive and negative controls)
Positive anti-IgA samples: Berlin 054 dilution 1/1-1/128
Positive anti-IgA samples: SRK Bern 7702 dilution 1/1-1/16
Negative anti-IgA samples: SRK 06.11.14 No 9991-9996

IgA Deficiency Test
ID-PaGIA IgA deficiency test KIT-ref 020701V (lot 45940.14.01) (including positive and negative controls)
Positive IgA deficiency samples: NO 2922-4279-TRINA-3632
Negative IgA deficiency samples: SRK Bern from 18.12.2014 NO 251-256
Human IgA: Jackson 009-000-011 lot 114820 4.7 mg/mL Syphilis Test
ID-PaGIA Syphilis antibody test Kit-ref 020401V (lot 45640901) (including positive and negative controls)
Positive Syphilis samples: Vitlalla 124644 dilution 1/1-1/2048
Negative anti-IgA samples: SRK 06.11.14 No 9991-9996

Method:

Addition of mineral oil in cards:

5 µL of mineral oil were dispensed in each microtube, above gel in corresponding cards. Cards were tested within 60 minutes after addition of oil.

Test Method:

The method was followed according to Instructions for Use:

10 µL of sample and 50 µL beads in card were dispensed

The incubation 5 minutes at Room Temperature took place

Centrifugation 10 minutes at 85 g was done

Cards were read on Banjo reader (version 2.18) and Saxo 2 reader version LOG-AK 01.00.12.

Tests were simultaneously lead on standard card (without oil) and on card with 5 µL mineral oil.

Results

Anti-IgA Test

The results are shown in FIG. 16.

IgA Deficiency Test

The results are shown in FIG. 17.

Syphilis Test

The results are shown in FIG. 18.

For all three tested PaGIA tests (i.e. ID-PaGIA anti-IgA, ID-PaGIA IgA Deficiency and ID-PaGIA Syphilis), addition of 5 µL of a low-density immiscible compound 102 as disclosed herein above gel supernatant did not change performances of tests. Strong positives reactions (pure sample) were slightly enhanced but without impact on titer. Additionally, presence of a low-density immiscible compound 102 as disclosed herein did not affect specificity.

The invention claimed is:

1. A device for detecting an analyte in a sample, the device comprising:
    a reaction chamber able to receive the sample;
    a separation matrix; and
    a layer composed of a low-density immiscible compound that separates the reaction chamber from the separation matrix,
    wherein the reaction chamber is located above the separation matrix within the device.

2. The device according to claim 1, wherein the separation matrix and/or the reaction chamber comprises an analyte ligand.

3. The device according to claim 2, wherein the analyte ligand is an antibody, an antibody fragment, or an antigen.

4. The device according to claim 1, wherein the low-density immiscible compound has a lower density than the density of the separation matrix.

5. The device according to claim 1, wherein the low-density immiscible compound has a density of less than 1, and/or the low-density immiscible compound is hydrophobic.

6. The device according to claim 1, wherein the low-density immiscible compound is a composition comprising one or more compounds selected from: synthetic oil, organic oil, mineral oil, paraffinic oil, paraffin, non-polar solvents, fatty acids, an alkane mixture and a pure alkane.

7. The device according to claim 1, wherein the low-density immiscible compound is liquid or solid at room temperature.

8. A method for detecting the presence of an analyte in a sample, the method comprising:
    a) providing a device according to claim 1;
    b) dispensing the sample into the reaction chamber of the device;
    c) exposing the device to sedimentation by gravitation and/or centrifugation;
    wherein reagents comprising an analyte ligand are provided at least at step a) and/or at step b); and
    identifying the presence of the analyte in the sample based on the formation of an analyte-ligand complex on or within the separation matrix after sedimentation, or
    identifying the absence of the analyte in the sample based on the lack of formation of the analyte-ligand complex on or within the separation matrix after sedimentation.

9. The method according to claim 8, wherein the low-density immiscible compound has a lower density than the density of the separation matrix.

10. The method according to claim 8, wherein the low-density immiscible compound is liquid or solid at room temperature.

11. The method according to claim 10, wherein the low-density immiscible compound is solid and the solid compound is liquefied thermally or chemically.

12. A kit for detecting an analyte in a sample, the kit comprising:
    a device comprising:
    a reaction chamber able to receive the sample;
    a separation matrix; and
    a layer composed of a low-density immiscible compound that separates the reaction chamber from the separation matrix,
    wherein the reaction chamber is located above the separation matrix within the device.

* * * * *